United States Patent [19]
Humphrey, Jr.

[11] Patent Number: 5,746,760
[45] Date of Patent: May 5, 1998

[54] SEMI-AUTOMATIC TISSUE MORCELLATION DEVICE

[75] Inventor: Louis E. Humphrey, Jr., San Jose, Calif.

[73] Assignee: Laserscope, San Jose, Calif.

[21] Appl. No.: 373,566

[22] Filed: Jan. 17, 1995

[51] Int. Cl.$^6$ ..................................... A61B 17/00
[52] U.S. Cl. ................ 606/171; 606/184; 128/753
[58] Field of Search ..................... 606/171, 170, 606/184, 180; 128/753–754

[56] References Cited

U.S. PATENT DOCUMENTS

| | | | |
|---|---|---|---|
| 4,258,716 | 3/1981 | Sutherland | 606/174 X |
| 4,848,338 | 7/1989 | De Satnick et al. | 606/171 X |
| 5,002,546 | 3/1991 | Romano | 606/180 X |
| 5,281,220 | 1/1994 | Blake, III | 606/170 X |
| 5,342,382 | 8/1994 | Brinkerhoff et al. | 606/184 |
| 5,509,918 | 4/1996 | Romano | 606/180 X |
| 5,522,830 | 6/1996 | Aranyi | 606/170 X |
| 5,556,416 | 9/1996 | Clark et al. | 606/170 X |

*Primary Examiner*—Michael Buiz
*Assistant Examiner*—Nancy Connolly Mulcare
*Attorney, Agent, or Firm*—Workman, Nydegger & Seeley

[57] ABSTRACT

The BTR device of the present invention preferably comprises a housing chamber with an attached hand grip and actuating ringlet positioned to be grasped and pulled toward the hand grip. Inside the housing chamber is a hollow, open-ended, helically-slotted cylindrical element having a diagonal groove formed within the outer surface. A travelling pin, attached to the actuating ringlet, is fitted within the diagonal groove such that movement of the actuating ringlet simultaneously moves the travelling pin and rotates the helically-slotted cylindrical element. Gear teeth on the helically-slotted cylindrical element engage gear teeth on an inner shaft element rotatably positioned within the helically-slotted cylindrical element such that rotation of the helically-slotted cylindrical element is transferred to the inner shaft element. Rotation of the inner shaft element simultaneously rotates an attached excision sleeve to permit smooth and simple cutting of a uniform tissue fragment which is then removed through the BTR device without the need to withdraw the BTR device from the surgical access site. A tension spring urges the released actuating ringlet to its original position when the pulling force is withdrawn thereby causing the helically-slotted cylindrical element to rotate reversely. The inner shaft element, and attached excision sleeve, however, do not reversely rotate due to a separating coil which prevents engagement of the gear teeth when the pulling force is withdrawn.

15 Claims, 3 Drawing Sheets

SEMI-AUTOMATIC TISSUE MORCELLATION DEVICE

BACKGROUND OF THE INVENTION

1. The Field of the Invention

The present invention relates to the field of endoscopic bulk tissue removal. More particularly, the present invention relates to methods and apparatus permitting easier and more rapid manual bulk tissue removal during endoscopic surgical procedures.

2. Prior State of the Art

Excision of tissue from within the intraabdominal cavity of a person may be indicated in various situations. For example, removal of cancerous tissue, such as a myoma, or of all or part of a diseased or damaged organ, such as a kidney, gall bladder, or uterus, may be necessary or desirable. In these situations, a minimally invasive endoscopic surgical procedure is often preferred.

For example, the excision of tissue may be performed laparoscopically by use of a Bulk Tissue Removal (BTR) instrument. Typically, the procedure involves inserting a veress canula into the abdominal cavity and performing an aspiration test to verify the ability to insufflate the intraabdominal cavity and create an operating field. If the aspiration test is satisfactory, a $CO_2$ gas insufflator is connected to the veress canula. The abdominal cavity is distended to a preselected intraabdominal pressure. A trocar and sheath is inserted directly into the abdominal cavity. The trocar is then removed and an endoscope is inserted, via the trocar sheath, into the intraabdominal cavity. After direct visualization of trocar sheath placement and an inspection of the intraabdominal cavity, the tissue to be excised is located. Additional trocar sheaths are then introduced into the abdominal cavity in various locations to allow introduction of numerous instruments to the endoscopic operating field.

In the case of a subserosal myoma, the myoma is grasped, rotated and lifted from the tissue infiltrated. The myoma is then cut away from the tissue. In the case of an intramural myoma, the tissue covering the myoma is first removed, then the myoma is excised as described above. The myoma tissue is then transected by use of a bulk tissue removal instrument and excised via the trocar sheath. In other types of tissue removal, such as removal of the uterus, the organ is severed and excised by use of a bulk tissue removal instrument. The tissue to be excised typically must be fragmented in some manner, such as by shearing or coring, to permit removal through a trocar sheath.

Shearing the tissue is done by means of a tissue punch. The tissue punch is a spring loaded device which the operator uses in a pistol grip fashion. The cutting edge is placed in direct contact with the tissue, the operator then closes the jaw and takes a small biopsy, approximately ½" square, of the tissue. These small samples are stored in the channel of the instrument. When the channel is filled, the tissue samples are removed by removing the tissue punch from the surgical access site and disassembling it. The punch is then reassembled and this process is repeated until the desired tissue is completely excised.

Disadvantages of shearing include time and effectiveness. When removing large samples of tissue, the shearing process takes a long period of time and can become very tedious for the operator. The tissue samples are a maximum of approximately ½" square pieces. In addition, when the tissue punch is applied to the tissue, the tissue tends to move away from the cutting edge making it difficult to stabilize the tissue in a position permitting the punch to operate efficiently. In particular, hard or calculus tissue can be extremely difficult to excise with the tissue punch.

As mentioned, coring is an alternative manner of fragmenting tissue. Coring the tissue is done by means of an excision or morcellation sleeve. The morcellation sleeve is a stainless steel tube with a distal cutting tip and a proximal tip with a collar that allows for gripping and rotation of the instrument. The tube is hollow with a sealing cap on the proximal tip which permits an instrument to pass through the hollow portion of the morcellation sleeve for grasping the tissue beyond the distal cutting tip. The grasped tissue is pulled toward the cutting edge, contact is made, and the collar is manually rotated. This rotating action cores the tissue and the cored samples are pulled into the sleeve. Because the sealing cap on the proximal tip is not large enough to allow removal of the grasping instrument while the tissue sample is held, the entire morcellation sleeve must be removed from the abdominal cavity so that the cored samples can be removed from the distal sleeve tip. This process, inserting the sleeve, grasping the tissue to be cut, rotating the collar to effect cutting, and withdrawing the sleeve to remove the tissue fragment, is repeated until the desired tissue is excised completely.

Disadvantages of coring include the required physical exertion by the surgeon, time and effectiveness. Physical exertion becomes a significant factor particularly during large tissue excisions. The operator often experiences symptoms similar to that of carpal tunnel syndrome due to the need to repeatedly manually rotate the cutting edge. The limited rotation in a single movement inhibits the effectiveness of this type of bulk tissue removal instrument and increases the time involved.

Additionally, both the shearing and coring excision methods require removal of the tissue fragmenting device from its position within the surgical access site through the abdominal cavity to effect removal of the tissue fragments. Typically, since only a small amount of tissue can be placed within the device, this insertion and removal of the device must be repeated many times thereby increasing the length of the entire procedure. Moreover, because the intraabdominal cavity is distended with $CO_2$ gas to a preselected pressure or pneumoperitoneum, there is a risk of loss of this pressure during insertion and removal of instruments. It can be seen that currently available shearing and coring devices which require repeated insertion and removal may cause loss of the desired pneumoperitoneum.

A percutaneous tissue removal apparatus having a powered flexible drill shaft attached to a cutting tip is disclosed in U.S. Pat. No. 5,269,785 issued to Bonutti, incorporated herein by reference. A powered drill-type apparatus, however, is prone to recoil causing accidental organ or tissue damage. Moreover, such an apparatus cannot be used in situations requiring more delicate handling, control and removal of tissue. For example, cancerous or diseased tissue must be completely and cleanly removed so as to avoid affecting healthy surrounding tissue. Such situations require that the instruments used in the surgical procedure operate as extensions of the surgeon's hands. In other words, the instruments should possess 1:1 hand to distal tip control of the instrument. Such a relationship does not exist in a powered drill-type apparatus.

BRIEF SUMMARY AND OBJECTS OF THE INVENTION

It is an object of the present invention to provide methods and apparatus permitting more rapid and efficient manual excision of tissue during an endoscopic surgical procedure.

It is another object of the present invention to provide methods and apparatus permitting smooth and consistent cutting of tissue with no recoil of the excision sleeve to eliminate the possibility of accidental tissue or organ damage during an endoscopic tissue excision procedure.

It is yet another object of the present invention to provide methods and apparatus permitting 1:1 hand to distal tip control of single direction ratchet-assisted rotation to decrease the time and physical exertion required to perform endoscopic tissue excision.

A further object of the present invention is to provide methods and apparatus permitting removal of fragmented tissue from within the intraabdominal cavity without requiring removal of the bulk tissue removal (BTR) device from the surgical access site thereby maintaining a desired pneumoperitoneum during an endoscopic tissue excision procedure.

Yet a further object of the present invention is to provide methods and apparatus adapted for use with various sized currently available manipulation instruments and various sized modified excision sleeves to effect more rapid and efficient manual excision of tissue during an endoscopic surgical procedure.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

To achieve the foregoing objects, and in accordance with the invention as embodied and broadly described herein, the BTR device of the present invention comprises a helix element, rotating means for rotating the helically-slotted cylindrical element about its cylindrical axis in a forward and reverse direction, an associated inner shaft element connected to an excision sleeve, and means for transferring rotation of the helically-slotted cylindrical element to the inner shaft element in one direction only such that rotation of the helically-slotted cylindrical element in the opposite direction is not transferred. In this manner, the cutting tip on the excision sleeve rotates unidirectionally to achieve smooth cutting of a uniform tissue fragment yet there is no recoil of the excision sleeve.

In a preferred embodiment of the present invention, the BTR device comprises a housing chamber with an attached hand grip. Also attached to the housing chamber is an actuating ringlet positioned to be easily grasped by the fingers when the BTR device is held by the hand grip. The actuating ringlet is slidably attached to the housing chamber such that the actuating ringlet can move toward the hand grip when pulled by the fingers. A travelling pin is attached to the actuating ringlet such that movement of the actuating ringlet toward the hand grip simultaneously moves the travelling pin. Inside the housing chamber is a hollow, open-ended, helically-slotted cylindrical element having a diagonal groove formed within the outer surface. One end of the travelling pin is fitted within the diagonal groove such that when the pin moves the helically-slotted cylindrical element is caused to rotate unidirectionally in place as the travelling pin is forced to track within the diagonal groove.

The helically-slotted cylindrical element has gear teeth on the inner surface of one end. An inner shaft element, also hollow, open-ended and cylindrical, fits rotatably within the helically-slotted cylindrical element. The ends of the inner shaft element extend through openings in the housing chamber. A collar attached to the inner shaft element has gear teeth positioned to engage the gear teeth on the helically-slotted cylindrical element. Accordingly, engagement of the facing gear teeth during rotation of the helically-slotted cylindrical element transfers that rotation to the inner shaft element in a ratchet-assisted manner. Before insertion of the BTR device into a surgical access site, an appropriately-sized excision sleeve, adapted to connect to the distal end of the inner shaft element, is selected and attached. The inner shaft element and attached excision sleeve define a hollow channel which permits insertion and removal of grasping, or other manipulation, instruments through the surgical access site. Moreover, unlike current tissue morcellation sleeves, the hollow channel also accommodates removal therethrough of tissue fragments held by a grasping instrument. Accordingly, the BTR device does not need to be withdrawn and reinserted through the surgical access site to remove tissue fragments. Rotation of the inner shaft element simultaneously rotates the attached excision sleeve. This ratchet-assisted rotation permits smooth and simple cutting of a uniform tissue fragment which is then removed through the hollow channel.

When the actuating ringlet is at rest, i.e., when no force is being applied, the attached travelling pin is positioned near one end of the diagonal groove of the helically-slotted cylindrical element. A rod, attached at one end to the actuating ringlet, extends slightly beyond the hand grip through a channel formed within the hand grip. The extending end of the rod is threaded such that a nut can be screwed on to the end. The nut can be threaded on to a selected position along the threaded portion of the rod such that the distance between the actuating ringlet and the hand grip is adjusted to be comfortable for the size of the operator's hand. A spring surrounds the rod between the actuating ringlet and the hand grip. As the actuating ringlet is pulled toward the hand grip, the spring tightens such that, upon release of the actuating ringlet, the spring returns the actuating ringlet to its resting position.

As the actuating ringlet returns to its resting position, the attached travelling pin also returns thereby causing the helically-slotted cylindrical element to rotate reversely in place as the pin backtracks within the diagonal groove. The inner shaft element, however, does not reversely rotate because of a separating coil positioned between the gear teeth on the helically-slotted cylindrical element and the facing gear teeth on the collar element. The separating coil prevents the facing gear teeth from engaging in the absence of sufficient pulling force on the actuating ringlet. Accordingly, as the actuating ringlet and helically-slotted cylindrical element return to their resting positions, the inner shaft element, and the attached excision sleeve, remain stationary. Thus, there is no recoil at the tissue cutting site. Subsequent grasping and pulling of the actuating ringlet repeats the entire process such that another uniform tissue fragment is easily and smoothly cut and then removed through the hollow channel.

BRIEF DESCRIPTION OF THE DRAWINGS

In order to more fully understand the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are therefore not to be considered limiting of its scope, the invention in its presently understood best mode for making and using the same will be described with additional specificity and detail through the use of the accompanying drawings in which.

DETAILED DESCRIPTION OF THE PREFERRED EMBODIMENTS

The present invention relates to the field of endoscopic bulk tissue removal. More particularly, the present invention relates to methods and apparatus permitting more rapid and efficient manual excision of tissue during endoscopic surgical procedures. The methods and apparatus of the present invention permit smooth and consistent single-direction ratchet-assisted rotation of a tissue excision sleeve with no recoil of the sleeve while also providing the surgeon with effective 1:1 hand-to-distal cutting-tip control. The methods and apparatus of the present invention further permit removal of fragmented tissue from within the intraabdominal cavity without requiring removal of a bulk tissue removal (BTR) device so that a desired intraabdominal pressure is maintained throughout the endoscopic tissue excision procedure.

The BTR device of the present invention comprises a helically-slotted cylindrical element, rotating means for rotating the helically-slotted cylindrical element about its cylindrical axis in both a clockwise and counter-clockwise direction, an associated inner shaft element connected to an excision sleeve, and means for transferring rotation of the helically-slotted cylindrical element to the inner shaft element in one direction only such that rotation of the helically-slotted cylindrical element in the opposite direction is not transferred. In this manner, the cutting tip on the excision sleeve rotates unidirectionally to achieve smooth cutting of a uniform tissue fragment and recoil of the excision sleeve is completely avoided.

Figure 1:
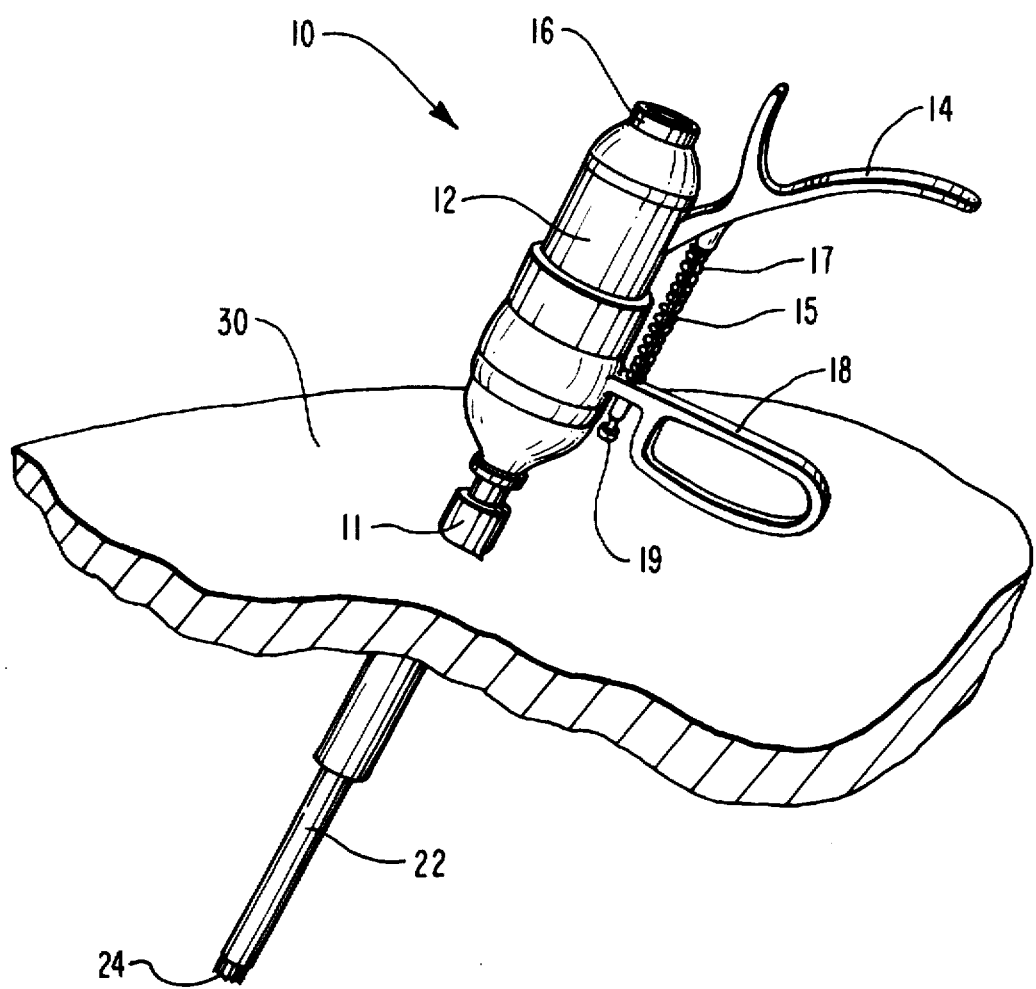
FIG. 1 is a schematic view of one preferred embodiment of the present invention positioned for use according to a preferred method of the present invention.

FIG. 1 schematically illustrates a preferred embodiment of the present invention positioned for use during an endoscopic bulk tissue removal procedure. The BTR device 10 preferably comprises a housing chamber 12. A hollow cylindrical inner shaft element 34 (shown in FIG. 3) is positioned within the housing chamber with both ends extending through openings in the housing chamber. The distal end is attached to an excision sleeve 22. The excision sleeve is preferably inserted through a trocar sheath 11 used to maintain a surgical access site formed through an abdominal wall 30. Trocar sheaths of various types are well known in the art. These are typically equipped with means for maintaining the intraabdominal pressure during the insertion and removal of various instruments such as the BTR device of the present invention.

The excision sleeve is hollow with a distal cutting tip 24 such that the hollow inner shaft element and the hollow excision sleeve define a continuous passage from outside the body into the intraabdominal surgical field. The proximal open end of the inner shaft element permits insertion and removal of grasping, or other manipulation, instruments and also accommodates removal therethrough of tissue fragments held by a grasping instrument. Excision sleeves of various sizes adapted to attach to the inner shaft element are preferably provided such that a surgeon can select the most appropriate sized sleeve for the particular procedure to be performed.

To prevent loss of intraabdominal pressure during the insertion and removal of instruments, the proximal open end of the inner shaft element is preferably equipped with a gas capturing seal 16, such as a conventional silicon triple seal gas capturing inlet or similar device. Accordingly, unlike current tissue morcellation sleeves, the BTR device of the present invention does not need to be withdrawn and reinserted through the surgical access site to remove tissue fragments. Rather, the BTR device is positioned as shown in FIG. 1 while the bulk tissue removal procedure is performed.

As shown in FIG. 1, a handgrip 14 is secured to the housing chamber near the proximal end. An actuating ringlet 18 is slidably attached to the housing chamber near the distal end and disposed with respect to handgrip 14 such that the actuating ringlet can be easily grasped by an operator's fingers when the operator's palm rests against the handgrip. The actuating ringlet can then be pulled toward the hand grip with an easy trigger-pull maneuver.

The present invention features bias means for urging the actuating ringlet to return to its "resting" position, i.e., its position when it is not being pulled, when the pulling force is removed or decreased. As shown in FIG. 1, a preferred embodiment of the present invention comprises a rod element 15 attached to handgrip 14 and extending through a channel formed through actuating ringlet 18. Rod 15 has a threaded end portion such that a nut 19 may be screwed onto the end. The distance between the actuating ringlet and the handgrip is adjustable to the degree that the nut may be variously positioned along the threaded portion of the rod. In this manner, the distance between the actuating ringlet and the handgrip can be adapted for the comfort and convenience of the particular operator. The portion of rod 15 between the actuating ringlet and the handgrip is surrounded by a tension spring 17 such that when the actuating ringlet is pulled toward the handgrip, the tension spring is compressed and, when the force on the actuating ringlet is removed or decreased, the tension spring urges the actuating ringlet to return to its resting position.

It will be understood by those of skill in the art that other bias means could also be used for urging the actuating ringlet to return to its resting position when the pulling force is removed or decreased. For example, a spring-loaded pivot pin or other conventional method could be used.

Figure 2:
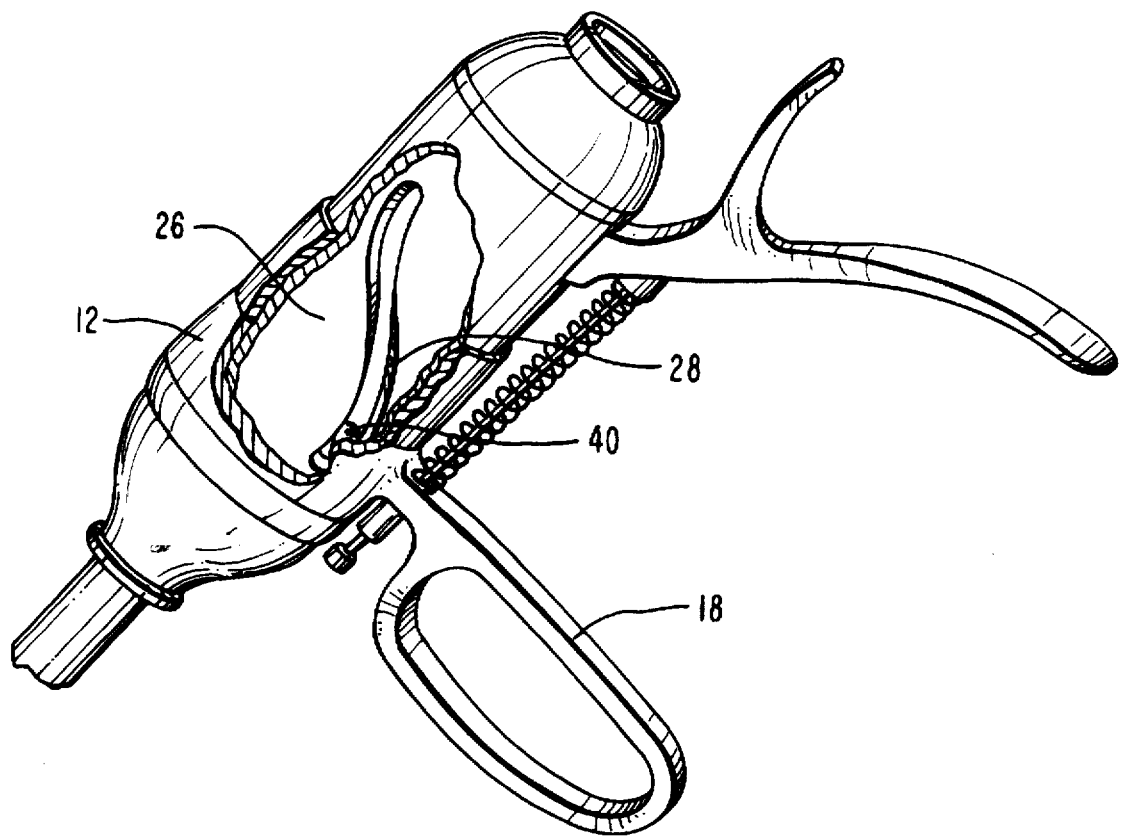
FIG. 2 is a detailed cut-away view of a housing chamber of the embodiment of FIG. 1.

FIG. 2 illustrates a cut-away view of a preferred embodiment of a housing chamber 12 in accord with the present invention. The present invention features rotation means for rotating a helically-slotted cylindrical element about its cylindrical axis in both a clockwise and counterclockwise direction. As shown in FIG. 2, a preferred embodiment of the present invention comprises a travelling pin 40 secured to the actuating ringlet 18. Travelling pin 40 is fittingly engaged within a diagonal groove 28 formed in the outer surface of a hollow, open-ended, helically-slotted cylindrical element 26 positioned within the housing chamber. Diagonal groove 28 tracks from a beginning point adjacent the distal end of the helically-slotted cylindrical element to an ending point adjacent the proximal end of the helically-slotted cylindrical element.

It can be seen that, as the actuating ringlet 18 is pulled toward the handgrip 14, the attached travelling pin also moves in an essentially linear distal-to-proximal direction thereby causing the helically-slotted cylindrical element to rotate in place about its cylindrical axis as the travelling pin travels within the diagonal groove. It can also be seen that, upon release of the actuating ringlet, as the actuating ringlet and attached travelling pin are urged by the bias means to return to their resting position. the helically-slotted cylindrical element also returns to its resting position by being rotated reversely in place as the pin backtracks within the diagonal groove.

Figure 3:
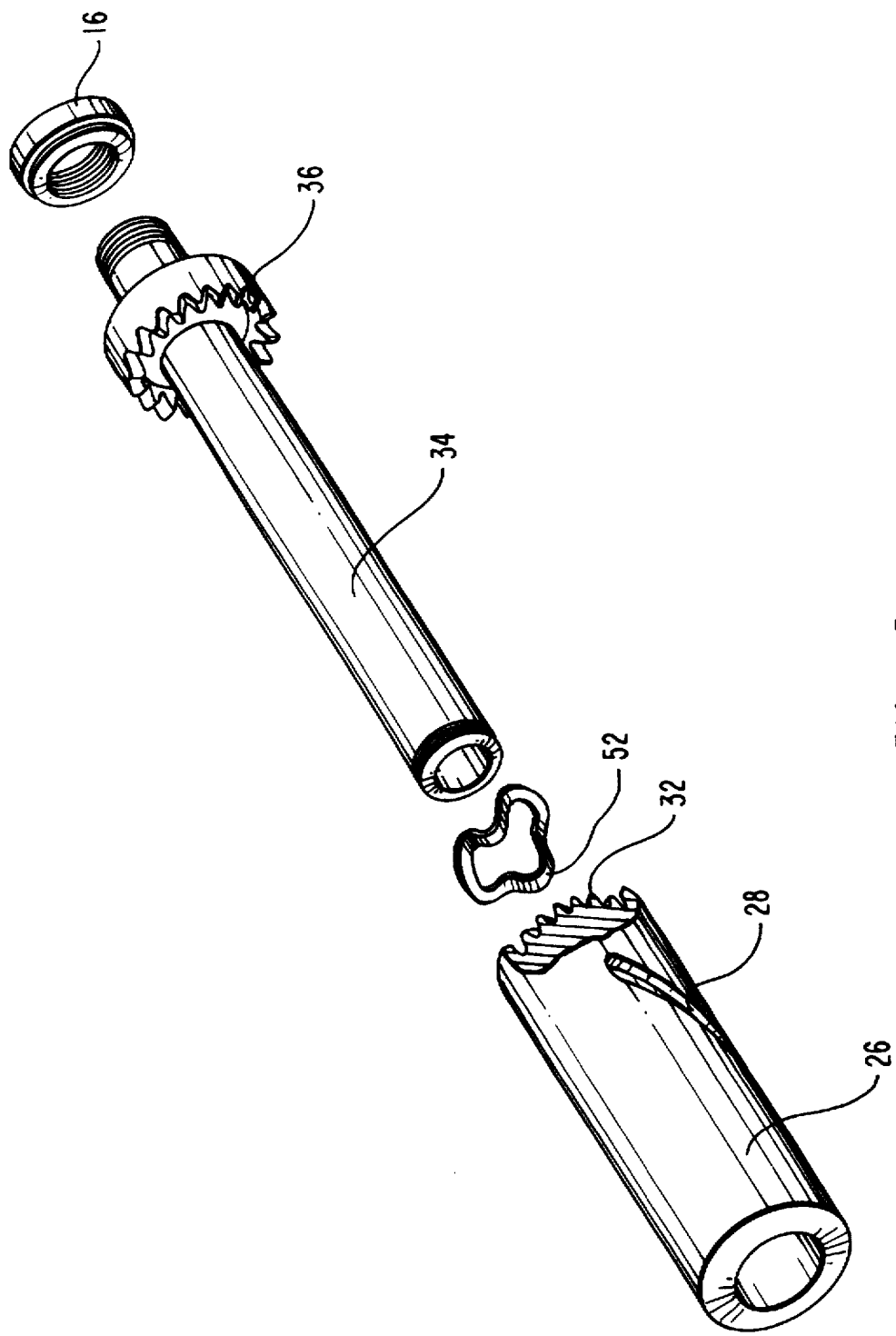
FIG. 3 is an exploded view of certain components of the embodiment of FIG. 1.

FIG. 3 illustrates an exploded view of certain elements of a preferred embodiment of the present invention. Another feature of the present invention is unidirectional rotation transfer means for transferring rotation of the helically-slotted cylindrical element to an inner shaft element during rotation of the helically-slotted cylindrical element in one direction but preventing transfer of rotation during rotation of the helically-slotted cylindrical element in the opposite direction. As described with respect to FIG. 1, a hollow, open-ended, cylindrical inner shaft element 34 is disposed within the housing chamber such that the ends of the inner shaft element extend through openings in the ends of the housing chamber. Also, as described with respect to FIG. 1, the proximal open end of the inner shaft element is adapted for fitting with a gas-capturing seal 16 and the distal open end is adapted for attachment of an excision sleeve 22 (shown in FIG. 1).

It should be understood that the distal open end of the inner shaft element is preferably adapted to accommodate attachment of variously-sized excision sleeves. This can be accomplished by known in the art methods such as providing variously-sized adapters to fit between the end of the inner shaft element and the variously-sized excision sleeve openings or by providing various-sized excision sleeves having identically-sized open ends for fitting onto the inner shaft element end.

As can be seen in FIG. 3, the inner shaft element is sized to be disposed within the helically-slotted cylindrical element 26 such that the helically-slotted cylindrical element is able to freely rotate about the inner shaft element 34. As described above with respect to FIG. 2, the helically-slotted cylindrical element has a diagonal groove 28 formed in the outer surface which engages a travelling pin attached to the actuating ringlet to rotate the helically-slotted cylindrical element in place about its cylindrical axis in one direction when the actuating ringlet is pulled toward the handgrip and in the opposite direction when the actuating ringlet is biased back to its resting position. The proximal end of helically-slotted cylindrical element 26 is shown partially cut-away in FIG. 3. As illustrated, the inner surface of the proximal end of the helically-slotted cylindrical element has gear teeth 32. A toothed collar element 36 is attached to the inner shaft element adjacent to the proximal end. When the inner shaft element is positioned within the helically-slotted cylindrical element, the gear teeth on toothed collar element 36 are positioned to engage the gear teeth on the helically-slotted cylindrical element. Engagement of the toothed collar element and gear teeth during rotation of the helically-slotted cylindrical element directly transfers the rotation of the helix element to the inner shaft element and thereby to the excision sleeve.

It should be understood that other arrangements of the gear teeth could also be used to permit direct transfer of rotation of the helically-slotted cylindrical element to the inner shaft element. For example, the toothed collar element could be sized such that the teeth would engage gear teeth positioned on the end of the helically-slotted cylindrical element or on the outer surface of the helix element rather than on the inner surface of the helically-slotted cylindrical element.

Engagement of the toothed collar element and gear teeth only occurs during rotation of the helically-slotted cylindrical element in one direction due to a separating coil 52 positioned between the toothed collar element and the gear teeth. When the actuating ringlet is pulled, the helically-slotted cylindrical element becomes squeezed against the toothed collar element. The separating coil is flattened by the squeezing pressure such that the toothed collar element and the gear teeth can engage each other. In this manner, the rotation of the helically-slotted cylindrical element while the actuating ringlet is being pulled is transferred to the inner shaft element. As described above with respect to FIG. 2, when the pulling force on the actuating ringlet is relaxed, the tension spring urges the actuating ringlet to return to its resting position and the helically-slotted cylindrical element is caused to rotate in the opposite direction and thereby also return to its resting position. In addition, when the pulling force on the actuating ringlet is relaxed, the separating coil is no longer being squeezed flat. Thus, the separating coil unflattens to thereby prevent the toothed collar element from engaging with the gear teeth. Thus, the rotation of the helically-slotted cylindrical element as it returns to its resting position is not transferred to the inner shaft element. Rather, the inner shaft element and the attached excision sleeve remain stationary such that there is no recoil at the tissue cutting site. Another pull on the actuating ringlet repeats the entire ratchet-assisted process such that another smooth and uniform slice is made in the contacted tissue. In this manner, uniform tissue fragments are easily and smoothly excised with minimal physical exertion by the operator.

It can be seen that rotation of the helically-slotted cylindrical element is transferred to the inner shaft element in one direction only, i.e., in a ratchet-assisted manner. Accordingly, each time the actuating ringlet is pulled to approach the handgrip as nearly as possible, the helically-slotted cylindrical element rotates while the gear teeth are engaged with the collar. Engagement of the gear teeth and collar transfers the rotation to the inner shaft element and the attached excision sleeve. The distal cutting tip of the excision sleeve is thereby rotated to achieve a smooth and uniform slicing effect in the contacted tissue. In this manner, a 1:1 hand-to-distal cutting-tip control is achieved.

It can be seen that the ratchet-assisted transfer of rotation to the inner shaft element permits easier and more rapid manual bulk tissue removal. The methods and apparatus of the present invention make it possible to remove an entire uterus in a 10–20 minute endoscopic procedure. Currently used BTR devices typically take significantly longer and require more physical exertion as well. Another advantage of the present invention is the provision of 1:1 hand-to-distal cutting-tip control. The unidirectional rotation of the inner shaft element and attached excision sleeve permits smooth and consistent cutting of tissue with no recoil thereby preventing accidental tissue or organ damage. Moreover, the BTR device of the present invention permits removal of tissue fragments without the need to remove the BTR device from the surgical access site.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Patent is:

1. A bulk tissue removal device comprising:

a helically-slotted cylindrical element having a hollow core therethough;

rotation means for rotating said helically-slotted cylindrical element about the cylindrical axis of said helically-slotted cylindrical element in either a clockwise or counterclockwise direction;

an inner shaft element rotatably positioned within the hollow core of the helically-slotted cylindrical element, said shaft element having a hollow core therethrough;

an excision sleeve adapted to connect to the inner shaft element, said sleeve having a cutting tip for cutting tissue; and unidirectional rotation transfer means for transferring rotation of the helically-slotted cylindrical element to the inner shaft element during rotation of the helically-slotted cylindrical element in one direction and preventing transfer of rotation of the helically-slotted cylindrical element to the inner shaft element during rotation of the helically-slotted cylindrical element in the opposite direction, wherein said unidirectional rotation transfer means facilitates smooth cutting of uniform tissue fragments without recoil of the cutting tip.

2. A bulk tissue removal device as described in claim 1 wherein the rotation means comprises:

a travelling pin fitted into a diagonal groove formed in the outer surface of the helically-slotted cylindrical element, said groove having a beginning distal point and an ending proximal point;

an actuating ringlet attached to the travelling pin, said actuating ringlet being originally positioned such that an applied force will move the actuating ringlet and attached travelling pin in a substantially linear distal-to-proximal direction relative to the helically-slotted cylindrical element to thereby force the diagonal groove to track against said travelling pin causing rotation of the helically-slotted cylindrical element in one direction; and bias means for returning the actuating ringlet, upon relaxation of the applied force, to its original position and thereby return the travelling pin to its original position such that the travelling pin moves in a substantially linear proximal-to-distal direction relative to the helically-slotted cylindrical element to thereby force the diagonal groove to backtrack against said travelling pin causing rotation of the helically-slotted cylindrical element in the opposite direction.

3. A bulk tissue removal device as described in claim 2 wherein the bias means comprises:

a handgrip positioned distal to the actuating ringlet such that the actuating ringlet may be grasped by the fingers and pulled toward the handgrip;

a rod element secured at a first end to the handgrip, said rod element passing through a channel formed in the actuating ringlet and having, a second end extending from said channel; and a tension spring surrounding the portion of the rod element between the handgrip and the actuating ringlet such that, when a pulling force is applied to move the actuating ringlet toward the handgrip, the tension spring compresses and, when the pulling force is relaxed, the tension spring urges the actuating ringlet to return to its original position.

4. A bulk tissue removal device as described in claim 3 wherein the second end of the rod element further comprises a threaded portion such that a nut may be threaded thereonto at a desired position to thereby adjust the distance between the handgrip and actuating ringlet to a selected span.

5. A bulk tissue removal device as described in claim 1 wherein the unidirectional rotation transfer means comprises:

gear teeth on the helically-slotted cylindrical element positioned to engage, during rotation of the helically-slotted cylindrical element in one direction, facing gear teeth attached to the inner shaft element;

a separating coil positioned between the facing gear teeth to prevent engagement of the gear teeth during rotation of the helically-slotted cylindrical element in the opposite direction.

6. A bulk tissue removal device comprising:

(1) a helically-slotted cylindrical element having a hollow core therethrough;

(2) rotation means for rotating said helically-slotted cylindrical element about the cylindrical axis of the helix element in either a clockwise or counterclockwise direction, said rotation means comprising:

(a) a travelling pin fitted into a diagonal groove formed in the outer surface of the helically-slotted cylindrical element, said groove having a beginning distal point and an ending proximal point;

(b) an actuating ringlet attached to the travelling pin, said actuating ringlet being originally positioned such that an applied force will move the actuating ringlet and attached travelling pin in a substantially linear distal-to-proximal direction relative to the helically-slotted cylindrical element to thereby force the diagonal groove to track against said travelling pin causing rotation of the helically-slotted cylindrical element in one direction; and (c) bias means for returning the actuating ringlet, upon relaxation of the applied force, to its original position and thereby return the travelling pin to its original position such that the travelling pin moves in a substantially linear proximal-to-distal direction relative to the helically-slotted cylindrical element to thereby force the diagonal groove to backtrack against said travelling pin causing rotation of the helically-slotted cylindrical element in the opposite direction;

(3) an inner shaft element rotatably positioned within the hollow core of the helically-slotted cylindrical element, said shaft element having a hollow core therethrough;

(4) an excision sleeve adapted to connect to the inner shaft element, said sleeve having a cutting tip for cutting tissue; and (5) unidirectional rotation transfer means for transferring rotation of the helically-slotted cylindrical element to the inner shaft element during rotation of the helix element in one direction and preventing transfer of rotation of the helically-slotted cylindrical element to the inner shaft element during rotation of the helically-slotted cylindrical element in the opposite direction, wherein said unidirectional rotation transfer means facilitates smooth cutting of uniform tissue fragments without recoil of the cutting tip.

7. A bulk tissue removal device as described in claim 6 further comprising a housing chamber for housing the helically-slotted cylindrical element.

8. A bulk tissue removal device as described in claim 7 further comprising a handgrip attached to the housing chamber and positioned to permit easy grasping of the actuating ringlet by an operator's fingers when the bulk tissue removal device is held in an operator's palm.

9. A bulk tissue removal device as described in claim 8 wherein the bias means comprises:
   a rod element secured at a first end to the handgrip, said rod element passing through a channel formed in the actuating ringlet and having a second end extending from said channel; and
   a tension spring surrounding the portion of the rod element between the handgrip and the actuating ringlet and the handgrip such that, when pulling force is applied to move the actuating ringlet toward the handgrip, the tension spring compresses and, when the pulling force is relaxed, the tension spring urges the actuating ringlet to return to its original position.

10. A bulk tissue removal device as described in claim 9 wherein the second end of the rod element further comprises a threaded portion such that a nut may be threaded thereonto at a desired position to thereby adjust the distance between the handgrip and actuating ringlet to a selected span.

11. A bulk tissue removal device as described in claim 10 wherein, upon positioning the bulk tissue removal device adjacent to a surgical access site such that the housing chamber is outside the body and the excision sleeve extends into the body, the inner shaft element and connected excision sleeve define a passage through which surgical instruments and tissue fragments may be passed.

12. A bulk tissue removal device as described in claim 6 wherein the unidirectional rotation transfer means comprises:
   gear teeth on the helically-slotted cylindrical element positioned to engage facing gear teeth attached to the inner shaft element during rotation of the helically-slotted cylindrical element in one direction; and
   a separating coil positioned between the facing gear teeth to prevent engagement of the gear teeth during rotation of the helically-slotted cylindrical element in the opposite direction.

13. A bulk tissue removal device as described in claim 12 wherein the separating coil flattens to permit engagement of the facing gear teeth when a pulling force is applied to the actuating ringlet and wherein the separating coil unflattens to prevent engagement of the facing gear teeth when the pulling force is relaxed.

14. A bulk tissue removal device comprising:
   (1) a helically-slotted cylindrical element having a hollow core therethrough;
   (2) rotation means for rotating said helically-slotted cylindrical element about the cylindrical axis of said helix element in a either a clockwise or counterclockwise direction, said rotation means comprising:
      (a) a travelling pin fitted into a diagonal groove formed in the outer surface of the helically-slotted cylindrical element, said groove having a beginning distal point and an ending proximal point;
      (b) an actuating ringlet attached to the travelling pin, said actuating ringlet being originally positioned such that an applied force will move the actuating ringlet and attached travelling pin in a substantially linear distal-to-proximal direction relative to the helically-slotted cylindrical element to thereby force the diagonal groove to track against said travelling pin causing rotation of the helically-slotted cylindrical element in one direction;
      (c) a handgrip positioned distal to the actuating ringlet such that the actuating ringlet may be grasped by the fingers and pulled toward the handgrip;
      (d) a rod element secured at a first end to the handgrip, said rod element passing through a channel formed in the actuating ringlet and having a second end extending from said channel; and
      (e) a tension spring surrounding the portion of the rod element between the handgrip and the actuating ringlet such that, when a pulling force is applied to move the actuating ringlet toward the handgrip, the tension spring compresses and, when the pulling force is relaxed, the tension spring urges the actuating ringlet to return to its original position;
   (3) an inner shaft element rotatably positioned within the hollow core of the helically-slotted cylindrical element, said shaft element having a hollow core therethrough;
   (4) an excision sleeve adapted to connect to the inner shaft element, said sleeve having a cutting tip for cutting tissue;
   (5) unidirectional rotation transfer means for transferring rotation of the helically-slotted cylindrical element to the inner shaft element during rotation of the helically-slotted cylindrical element in one direction and preventing transfer of rotation of the helically-slotted cylindrical element to the inner shaft element during rotation of the helically-slotted cylindrical element in the opposite direction, said unidirectional rotation means comprising:
      (a) gear teeth on the helically-slotted cylindrical element positioned to engage facing gear teeth attached to the inner shaft element during rotation of the helically-slotted cylindrical element in one direction; and
      (b) a separating coil positioned between the facing gear teeth to prevent engagement of the gear teeth during rotation of the helically-slotted cylindrical element in the opposite direction wherein the separating coil flattens to permit engagement of the facing gear teeth when sufficient pulling force is applied to the actuating ringlet and the separating coil unflattens to prevent engagement of the facing gear teeth in the absence of sufficient pulling force applied to the actuating ringlet.

15. A bulk tissue removal device as described in claim 14 wherein the second end of the rod element further comprises a threaded portion such that a nut may be threaded thereonto at a desired position to thereby adjust the distance between the handgrip and actuating ringlet to a selected span.

\* \* \* \* \*